(12) United States Patent
Marcher et al.

(10) Patent No.: US 9,101,936 B2
(45) Date of Patent: Aug. 11, 2015

(54) SEALED OXYGEN REFERENCE FLUID CONTAINING BAG

(75) Inventors: Ib Marcher, Herlev (DK); Henrik Siiger, Virum (DK); Allan Spork, Kongens Lyngby (DK)

(73) Assignee: Radiometer Medical ApS, Bronshol (DK)

( * ) Notice: Subject to any disclaimer, the term of this patent is extended or adjusted under 35 U.S.C. 154(b) by 1478 days.

(21) Appl. No.: 12/081,996

(22) Filed: Apr. 24, 2008

(65) Prior Publication Data

US 2008/0279487 A1    Nov. 13, 2008

(30) Foreign Application Priority Data

Apr. 27, 2007   (EP) ..................................... 07388027

(51) Int. Cl.
| | | |
|---|---|---|
| *B65D 33/24* | (2006.01) | |
| *B01L 3/00* | (2006.01) | |
| *B65D 41/00* | (2006.01) | |
| *B65D 30/00* | (2006.01) | |
| *B65D 51/00* | (2006.01) | |
| *B65D 75/58* | (2006.01) | |
| *G01N 33/96* | (2006.01) | |
| *B65D 33/16* | (2006.01) | |

(52) U.S. Cl.
CPC ............... *B01L 3/505* (2013.01); *B65D 51/002* (2013.01); *B65D 75/58* (2013.01); *G01N 33/96* (2013.01); *B01L 3/50* (2013.01); *B01L 3/50825* (2013.01); *B01L 2200/025* (2013.01); *B01L 2200/026* (2013.01); *B01L 2200/0689* (2013.01); *B01L 2300/04* (2013.01); *B01L 2300/041* (2013.01); *B01L 2300/044* (2013.01); *B01L 2300/0848* (2013.01); *G01N 2496/70* (2013.01)

(58) Field of Classification Search
USPC .......................................... 383/200; 422/555
See application file for complete search history.

(56) References Cited

U.S. PATENT DOCUMENTS

| | | | | |
|---|---|---|---|---|
| 4,010,786 | A | | 3/1977 | Aguettant et al. ............. 383/202 |
| 4,078,699 | A | * | 3/1978 | Soto ................................ 222/89 |
| 4,325,496 | A | * | 4/1982 | Malpas ........................... 222/83 |
| 5,114,004 | A | * | 5/1992 | Isono et al. .................... 206/222 |
| 5,137,527 | A | * | 8/1992 | Miller et al. .................. 604/415 |
| 5,163,909 | A | * | 11/1992 | Stewart ......................... 604/140 |
| 5,465,768 | A | * | 11/1995 | DeRoos et al. ............... 141/329 |
| 5,732,853 | A | | 3/1998 | Ganzeboom et al. ........... 222/82 |
| 5,777,202 | A | * | 7/1998 | Betts et al. ..................... 73/1.03 |
| 5,780,302 | A | | 7/1998 | Conlon et al. |
| 6,632,675 | B1 | | 10/2003 | Conlon et al. |

(Continued)

FOREIGN PATENT DOCUMENTS

| | | |
|---|---|---|
| FR | 2593144 A | 7/1987 |
| GB | 1300461 A | 12/1972 |

(Continued)

*Primary Examiner* — Jennifer Wecker
(74) *Attorney, Agent, or Firm* — Finnegan, Henderson, Farabow, Garrett & Dunner, LLP

(57) ABSTRACT

The invention relates to a sealed oxygen reference fluid containing bag adapted for being pierced by an access probe for withdrawal of the oxygen reference fluid and including an access system comprising: a sealing element provided outside the bag and preventing any leakage between the bag and the access probe when the access probe has penetrated the bag, and a longitudinal support element provided inside the bag extending essentially parallel to an edge of the bag and being adapted to support the bag when the bag is penetrated by the access probe.

30 Claims, 3 Drawing Sheets

(56) References Cited

U.S. PATENT DOCUMENTS

| | | |
|---|---|---|
| 6,835,571 B2 | 12/2004 | Conlon et al. |
| 2004/0001655 A1 | 1/2004 | Proicou et al. |
| 2004/0047771 A1* | 3/2004 | Conlon et al. ................ 422/102 |
| 2005/0121464 A1* | 6/2005 | Miller et al. .................... 222/81 |
| 2005/0194060 A1* | 9/2005 | Houwaert et al. ............ 141/114 |
| 2005/0239199 A1* | 10/2005 | Kunas et al. ................ 435/297.1 |
| 2006/0188182 A1* | 8/2006 | Moteki et al. ................ 383/200 |
| 2006/0287633 A1* | 12/2006 | Yo ................................ 604/317 |
| 2007/0027437 A1* | 2/2007 | Burg et al. .................... 604/415 |
| 2007/0060903 A1* | 3/2007 | Miyajima et al. ............. 604/410 |

FOREIGN PATENT DOCUMENTS

| | | |
|---|---|---|
| JP | 02-176462 | 7/1990 |
| JP | 4-16346 U | 2/1992 |
| WO | WO 99/40430 | 8/1999 |
| WO | WO 2006/005347 A | 1/2006 |
| WO | WO 2006005347 A1 * | 1/2006 |

* cited by examiner

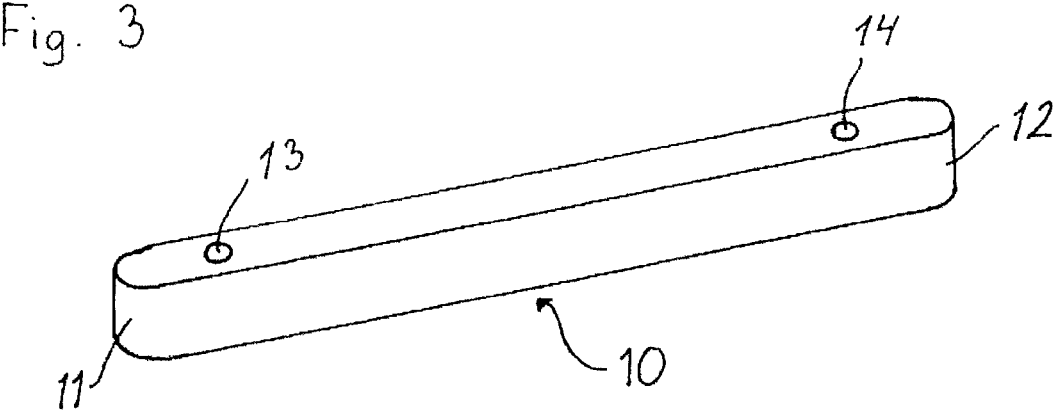
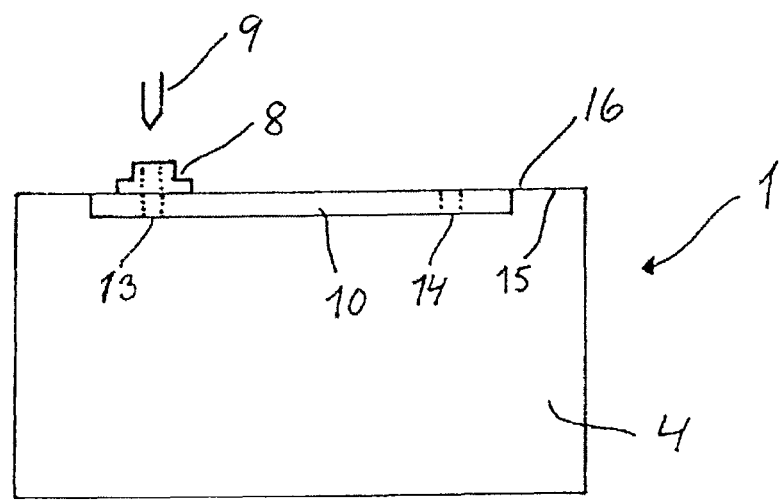

SEALED OXYGEN REFERENCE FLUID CONTAINING BAG

The invention relates to a sealed oxygen reference fluid containing bag adapted for being pierced by an access probe for withdrawal of the oxygen reference fluid and including an access system.

Bags for reference fluids are widely used in connection with analytical instruments. The bags are frequently delivered in containers, e.g. a cassette, wherein several bags are delivered in one cassette. A single cassette may comprise several different reference fluids depending on the analytical instrument the cassette is adapted to deliver reference fluids to.

The analytical instrument may be an instrument for measuring on body fluids such as blood. Typical parameters measured on blood are, for example, $pCO_2$, $pO_2$, pH, $Na^+$, $K^+$, $Ca^{2+}$, $Cl^-$, glucose, lactate, creatinine, bilirubin and hemoglobin values, such as $FO_2Hb$, FCOHb, FMetHb, FHHb and FHbF. Sensors typically measure the parameters and each parameter normally requires a specific sensor. However, to provide reliable results, the sensors need to be calibrated frequently. The calibration is carried out using reference fluids, which may be gaseous or liquid, and the process of calibration is well-known to the skilled person.

One particular reference fluid comprising oxygen used for the calibration of oxygen sensors causes special problems. The bag has to be substantially airtight in order to keep the desired concentration of oxygen. If oxygen diffuses through the material of the bag this will effect a change in the concentration of oxygen and the reference fluid may not be suitable for calibration. Thus, glass bottles or pressure bottles have traditionally been used as containers for oxygen reference fluid. However, a development of comparatively recent date has made it possible to deliver and store oxygen reference fluids in bags made from flexible laminar material, e.g. aluminum foil lined with one or more polymers.

Leakage of gas is particularly a pronounced problem when the flexible wall of the bag is penetrated by an access probe for withdrawal of reference fluid for calibration into an analytical instrument. When the bag wall has been broken by the access probe an effective sealing between the wall and the access probe is required to avoid leakage.

U.S. Pat. No. 5,780,302, U.S. Pat. No. 6,632,675, and U.S. Pat. No. 6,835,571 disclose a bag where a sealing member is attached to the inner surface of the bag at the location where the access probe penetrates the wall of the bag. However, the method requires rather complicated means to ensure that the access probe breaks the wall on the right spot, and measures need to be taken to ensure that the penetrating access probe does not loosen the sealing element from the wall and destroy the sealing effect. Although a satisfactory sealing may be obtainable in the aforementioned way an even better sealing is desirable in order to obtain a prolonged life of the reference fluid when the wall of the bag has been broken.

An object of the present invention is to provide an improved sealing between the wall of the bag and the access probe.

The invention provides a sealed oxygen reference fluid containing bag which bag may be penetrated by an access probe while gas leakage due to the build-in sealing system is substantially avoided.

The invention further provides a bag included in a container that facilitates the supply of reference fluid to an analyzing instrument. Moreover, the container is easy to replace in the analyzing instrument, whereby the reference fluid also is easy replaced.

Thus, in the sealed bag according to the invention the access system comprises a sealing element provided outside the bag and preventing any leakage between the bag and the access probe when the access probe has penetrated the bag, and a longitudinal support element provided inside the bag extending essentially parallel to an edge of the bag and being adapted to support the bag when the bag is penetrated by the access probe.

The access probe provides the connection between the oxygen reference fluid in the bag and a sensor element that requires calibration.

As the sealing element is provided on the exterior of the bag and the access probe passes through the sealing element, the movement of the access probe during piercing of the bag forces the sealing element towards the exterior wall of the bag and provides an even tighter sealing. This is in contrast to the prior art technique where the sealing element is provided on the interior wall of the bag. This prior known location of the sealing element has the consequence that the movement of the access probe during piercing of the bag may accidental loosen the sealing element from the wall of the bag.

The support element is adapted to support the walls of the bag, e.g. during mounting in a container. However, to fulfill the properties to serve as support, the support element is preferably made from a rather rigid material and, therefore, not capable to function as sealing element, when the bag is pierced by an access probe. Consequently, a sealing element is required to seal the bag subsequent to piercing by an access probe. The support element may also serve as a support for the sealing element when the access probe penetrates the wall of the bag whereby a very tight sealing between the sealing element and the wall of the bag is obtained.

The support element preferably is completely enclosed in the bag without penetrating the walls of the bag. More preferred the support element is attached to an inner surface portion of the bag. The support element is a longitudinally bar-like element having dimensions to make it fit within a bag without penetrating the walls of the bag. Moreover, the support element preferably has rounded ends to avoid damaging of the walls of the bag.

The sealing element has a shape that makes it possible to obtain a tight sealing between the access probe and the wall of the bag, and the sealing element preferably has a substantially cylindrical form that enclose the access probe and a flange that abut against the wall of the bag on the place of piercing. To obtain the desired flexibility the sealing element is preferably made from rubber material e.g. butyl rubber. In case of more access probes and more bags being placed in a container, more sealing elements are required. The sealing elements may be mutually connected to facilitate mounting in the container.

In a preferred embodiment of the bag according to the invention the sealing element is attached to an outer surface of the bag. The sealing element is naturally attached to the bag at the location where the access probe pierces the bag, and the sealing element subsequent by interaction with the access probe and the wall of the bag seals the opening produced by the piercing. The sealing element may be attached to the surface by means of glue or by melting of the material of the sealing element and the bag. The glue or melted material may serve as additional sealing material and provide a tighter sealing.

In an alternative preferred embodiment of the bag according to the invention the sealing element is attached to the access probe. In this embodiment the sealing element follows the access probe and the sealing element seals the produced opening by interaction with the access probe and the wall of the bag. Leakage after piercing due to an imprecise placement of the sealing element on the surface of the bag may be avoided as the sealing element is placed on the surface of the bag by the access probe during piercing. The sealing element may adhere to the access probe simply by friction.

In a further alternative preferred embodiment of the bag the sealing element is attached in a frame like structure between the access probe and the wall of the bag optionally abutting the wall of the bag. The sealing element is attached in such a way that the access probe easily may enter the sealing element, penetrate the wall of the bag and simultaneously press the sealing element towards the wall of the bag. The frame-like structure for holding the sealing element is preferably attached within a box-like structure holding one or more assemblies according to the invention.

During piercing of the bag the support element has the further function of supporting the wall of the bag and interacts with the access probe and the sealing element to obtain a very tight sealing.

For the purpose of achieving an easy attachment of the support element to the surface portion of the wall, in a preferred embodiment the support element and the inner surface portion of the bag are made from the same material. When the support element and the surface portion of the wall are made of the same material they may easily be jointed e.g. by melting or gluing the material. The material is preferably a polymer, e.g. polyethylene or polypropylene.

The support element conveniently comprises at least one passage adapted to interact with a penetrating access probe. Preferably an inner wall in the support element forms the passage which is substantially non-deformable. The passage preferably has a diameter that exceeds the diameter of the access probe, which allows the access probe easily to enter the passage. The passage typically has a diameter being 2 to 10% larger than the diameter of the access probe. Consequently, the support element has no sealing effect. However, the support element with the passage provides for the sealing element being placed in close contact with the exterior wall of the bag, while the interior wall is supported by the support element in such a way that the piercing access probe forces the sealing element towards the exterior wall of the bag.

The support element may comprise at least two through-going holes or bores arranged at opposite ends of the support element. This makes the support element substantially symmetric which facilitate the mounting in the bag.

Alternatively the support element comprises a plurality of through-going holes or bores at the respective opposite ends of the support element. This embodiment also facilitates the mounting and provides more freedom for placing the point for piercing.

In a preferred embodiment of the bag, one or both ends of the support element are provided with tongues. The one or two tongues are adapted to be cast into one or two welded joints of the bag. The embodiment provides for a more stable attachment of the support element to the bag and reduces the risk of breaching the wall of the bag due to movement of the support element, e.g. during transport of the bag.

The dimensions of the support element naturally depends on the specific use, however, a preferred length is from about 10 cm to about 22 cm, more preferred from about 13 cm to about 18 cm. Preferably the support element has a cross section area in the range of about 0.5 cm$^2$ to about 3 cm$^2$, more preferred from about 0.7 cm$^2$ to about 1.5 cm$^2$. The cross section of the support element may be substantially circular, oval, square, rectangular or any other desired shape.

As the inner wall of the passage is substantially non-deformable, the risk of displacing the support element by means of the access probe during the insertion of the access probe in the bag and thus leading to leakage is minimized. It may be that the support element as such is substantially non-deformable. The support element is preferably made from a polymer material such as polyethylene, polypropylene or similar material from which relatively rigid or non-deformable elements may be produced. In a preferred embodiment, the support element is made of polyethylene.

It is preferred that the bag comprises multiple laminated layers comprising an inner layer of a heat-sealable polymer. By using a heat sealable polymer as the inner layer it is possible to obtain a tight sealing of the inner surface of the bag and thereby a tight sealed bag by heat-welding the surfaces of heat-sealable polymer. Examples of suitable heat-sealable polymers are polyethylene and polypropylene. In a preferred embodiment the inner layer is made from polyethylene, which is easy to heat-weld.

In order to obtain a gas tight and durable bag the multiple laminated layers preferably comprise aluminum. Aluminum, suitable in the form of an aluminum foil, provides gas tightness and strength to the laminated material.

Preferably the bag is in the form of an envelope, which makes it easier to fit more bags into a container. Moreover, the envelope shape also provides for an optimal utilization of the space in the container.

Consequently, in a preferred embodiment the bag is included in a container. The container is preferably a box-like container having a lid and comprising one or more bags and wherein at least one of the bags contains an oxygen reference fluid. The container is conveniently made from a plastic material e.g. acrylonitrile-butadiene-styrene (ABS), polyethylene (PE) or polycarbonate (PC). The container e.g. includes 6-12 bags of which some or all may contain oxygen. However, some bags may also contain other calibration or rinse fluids.

In a preferred embodiment the one or more access probes are formed integrally with the lid of the container. The number of access probes integrated in the lid suitable corresponds to the number of bags in the container. The access probes may be formed by any conventional means, e.g. dye casting or mold forming. The access probes are preferably made from a plastic material that is gas tight, suitable for laser welding and has a suitable strength and rigidity to penetrate the bags, e.g. from acrylonitrile-butadiene-styrene (ABS), polyethylene terephthalate (PETP) or thermoplastic polyester (PET).

The container preferably comprises a snap-fit for securing the lid to the remainder or box-like part (although it may have any desired cross-section, such as square, circular, oval etc., the lid is of course adapted to fit the shape of the remainder). In one embodiment the container is provided in a non-secured state and the user activates the snap-fit function just before the container is to be utilized, optionally by removal of a safety device. Use of a safety device may serve to protect against unintended piercing of the bags as the activation of the snap-fit function will also cause the one or more access probes to penetrate the one or more bags in the container. As the access probes penetrate the one or more bags the one or more produced openings are simultaneously sealed by the sealing elements.

Consequently, in a preferred embodiment the access probe does not pierce the bag when the lid is not secured to the remainder of the container, however, the access probe pierces the bag when the lid is secured to the remainder of the container.

In a further embodiment the sealing element is provided in a frame-like structure attached to the container. As the sealing element may be integrated with the access probe, the sealing element may also be integrated in the lid of the container, thus, the invention also encompasses an embodiment of the container where the sealing element is provided in a lid of the container. The lid may be the lid incorporating the access probe or if e.g. production requires it may be a separate lid.

The invention will now be described in further details with reference to examples and drawings in which:

FIG. 3 shows an example of a support element according to the invention.

FIG. 4 shows a cut through a bag with the mounted support element.

Figure 1:
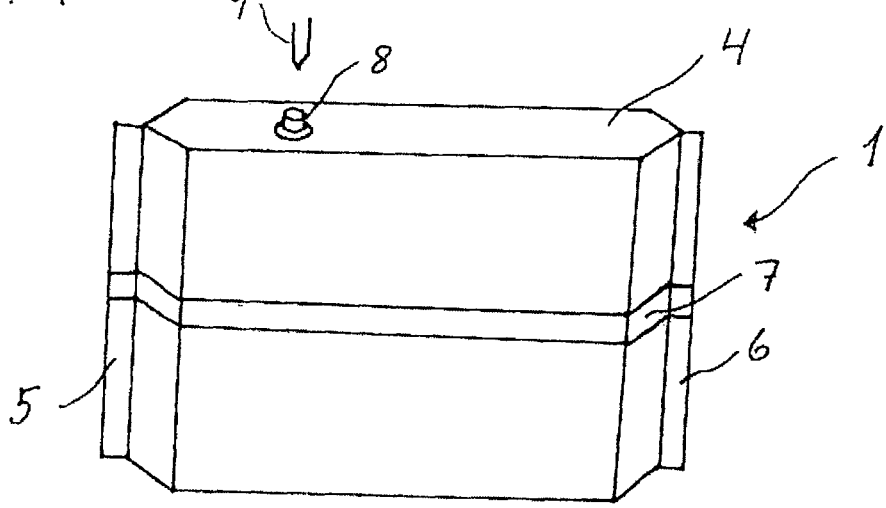
FIG. 1 shows a bag with an access system according to the invention.

FIG. 1 shows a simplified depiction of a bag with an access system according to the invention. The bag with access system 1 comprises a sealed bag 4 shaped as an envelope and containing an oxygen reference fluid and a support element (not visible). The bag 4 is manufactured from a heat-sealable foil consisting of an inner layer of polypropylene (PP70) with about 70 μm thickness, a diffusion barrier layer of aluminum, with a thickness of about 9 μm, and outer layer of polyethylene terephtalate (PETP) with a thickness of about 12 μm, for protecting the other layers and for providing a better basis for labelling, increasing the rigidity of the laminate etc. The bag has heat-sealed joints 5, 6 at the end-parts and along the side 7 of the bag 4. The access system 1 is furthermore provided with a sealing element 8 capable of sealing an opening in the bag pierced by an access probe 9 as indicated in the upper part of the figure. The access probe 9 may be connected to a lid or other element (not shown) of a container. The sealing element is made from butyl rubber and the access probe is made from ABS.

Figure 2:
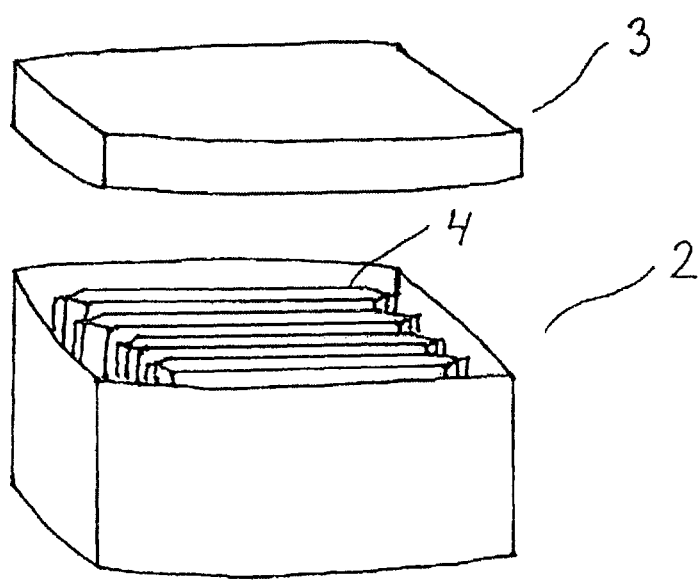
FIG. 2 shows a container according to the invention.

FIG. 2 shows a container 2 in the shape of a box-like member 2 and lid 3. The box-like member and the lid is made from ABS. The box-like member 2 contains several bags of which at least one is a bag 1 according to the invention. The lid 3 may comprise access probes (not shown) for piercing the bags 4 and further devices (not shown) for connecting the bags 4 to e.g. a blood-analyzing instrument.

FIG. 3 depicts a support element 10 for use in a bag 4 according to the invention. The support element 10 is shaped as a longitudinally element with rounded ends 11, 12. Furthermore the support element 10 is equipped with passages in the form of holes 13, 14 symmetrically at each end. The holes 13, 14 are intended to receive an access probe for withdrawal of oxygen. Indeed, one hole would be sufficient, however, the two holes 13, 14 made symmetrically in each end of the support element facilitate the production and mounting of the support element 10.

In FIG. 4 a support element 10 is seen mounted in the interior of a bag 4. The support element 10 is mounted on the inner wall 15 of the bag 4. On the outer wall 16 of the bag 4 is mounted a sealing element 8 at the location of the hole 13 in the support element 10.

In conjunction, the sealing element 8 and the hole 13 may receive an access probe 9 intended to withdraw fluid from the bag 4 and seal the opening that results from the piercing of the access probe 9.

Figure 5:
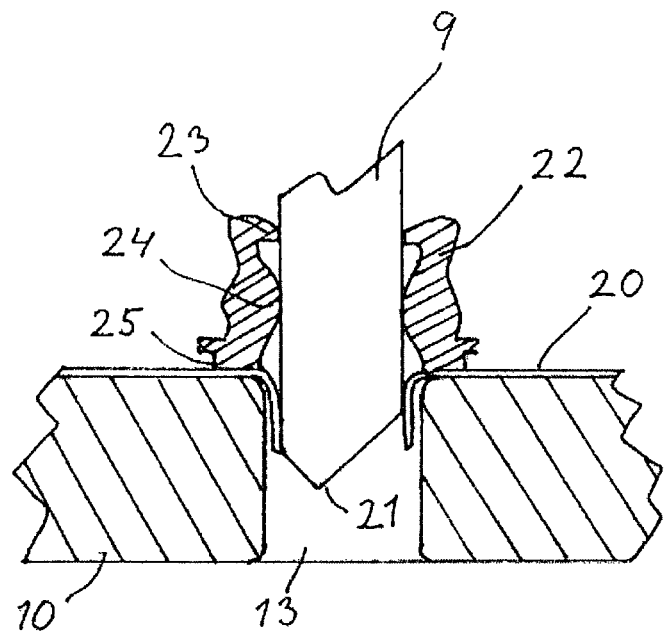
FIG. 5 shows an embodiment of a sealing element.
Figure 6:
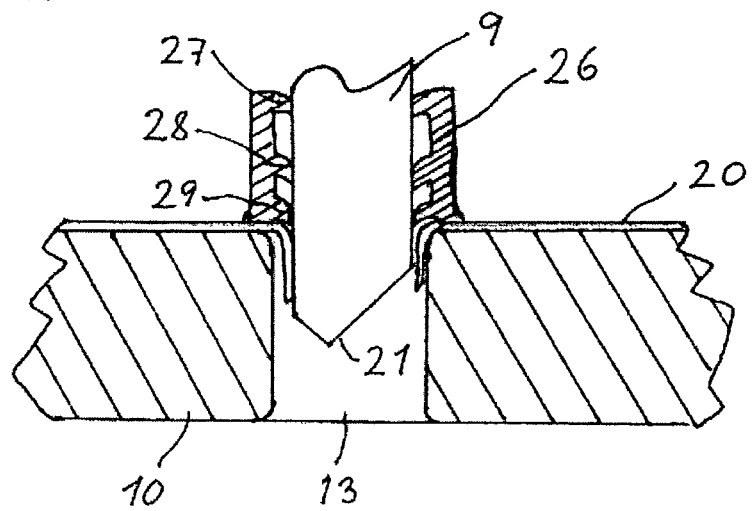
FIG. 6 shows a second embodiment of a sealing element.

FIGS. 5 and 6 show two embodiments of a sealing element during the sealing of a bag.

FIG. 5 shows a bag wherein an access probe 9 pierces the wall 20 of the sealed bag. The wall 20 is supported by a support element 10 at the place of piercing in such a way that a hole 13 in the support element 10 receives the tip 21 of the access probe 9. A sealing element 22 surrounds the access probe 9 with tight connections 23, 24 caused by the access probe 9 deforming the sealing element 22 during piercing. The sealing element 22 also comprises a flange 25 abutting the wall 20 of a bag. The tight connections 23, 24 and the flange 25 ensure a tight sealing of the opening made by the access probe 9. A similar arrangement is shown in FIG. 6, which only differs from FIG. 5 in the design of the sealing element 26. The sealing element 26 comprises three tongues 27, 28, 29 that provide a tight sealing around the access probe 9.

When the access probe 9 has pierced the wall 20 of a bag as shown in FIGS. 5 and 6, the access probe 9 also forces the sealing element 22, 26 to a tighter abutment with the wall 20 of a bag. This tighter abutment is mainly achieved by the movement of the access probe 9 through the sealing element 22, 26 towards the wall 20 of a bag.

Thus, it may be seen that it is the interaction between the access probe 9, the sealing element 26, the wall of the bag 20 and the support element 10 that provides the unexpected tight sealing.

The invention claimed is:

1. A reference fluid bag assembly, comprising:
   a sealed bag comprising oxygen reference fluid; and
   an access system comprising:
      a sealing element,
      an access probe,
      wherein the sealing element defines an access location for accepting the access probe and wherein the access probe is configured to pass through the access location and penetrate the sealed bag through an exterior wall to withdraw at least a portion of the oxygen reference fluid from the sealed bag, and wherein the access probe forces the sealing element towards the exterior surface of the sealed bag when penetrating the sealed bag, and
      a longitudinal support element attached to an internal surface of the bag without penetrating the bag and extending essentially parallel to the internal surface of the bag and wherein the longitudinal support element comprises at least one opening,
      wherein the longitudinal support element is disposed substantially opposite the sealing element and the access probe is configured to pass through the at least one opening of the longitudinal support element after penetrating the sealed bag.

2. The bag assembly according to claim 1, wherein the sealing element is attached to an outer surface of the sealed bag.

3. The bag assembly according to claim 1, wherein the sealing element is attached to the access probe.

4. The bag assembly according to claim 1, wherein the sealing element is attached in a frame structure between the sealed bag and the access probe.

5. The bag assembly according to claim 4, wherein the sealing element abuts the external surface of the bag.

6. The bag assembly according to claim 1, wherein the longitudinal support element and said internal surface portion of the sealed bag are made from the same material.

7. The bag assembly according to claim 1, wherein an inner wall forming the at least one opening of the longitudinal support element is substantially non deformable.

8. The bag assembly according to claim 1, wherein the longitudinal support element comprises a tongue in at least one end, said tongue being adapted to be cast into a joint of the sealed bag.

9. The bag assembly according to claim 1, wherein the sealed bag comprises multiple laminated layers comprising an inner layer of a heat-sealable polymer.

10. The bag assembly according to claim 9, wherein the heat-sealable polymer is polyethylene.

11. The bag assembly according to claim 9, wherein the multiple laminated layers comprise aluminum.

12. The bag assembly according to claim 1, wherein the sealed bag is in the form of an envelope.

13. The bag assembly according to claim 1, further comprising a container, wherein the sealed bag is included in the container.

14. The bag assembly according to claim 13, wherein the container holds a plurality of sealed bags and one or more access probes.

15. The bag assembly according to claim 14, wherein the one or more access probes are formed integrally with a lid of the container.

16. The bag assembly according to claim 15, wherein the lid and a remainder of the container comprise a snap-fit for securing the lid to the remainder of the container.

17. The bag assembly according to claim 16, wherein the access probe is separate from the bag when the lid is unsecured to the remainder of the container, and wherein the access probe pierces the bag when the lid is secured to the remainder of the container.

18. The bag assembly according to claim 13, wherein the sealing element is provided in a frame structure attached to the container.

19. A container comprising:
a lid;
a sealed bag comprising oxygen reference fluid; and
an access system comprising:
a sealing element,
an access probe provided with the lid, wherein the sealing element defines an access location for accepting the access probe and wherein the access probe is configured to pass through the access location and penetrate the sealed bag through an exterior wall to withdraw at least a portion of the oxygen reference fluid from the sealed bag, and wherein the access probe forces the sealing element towards the exterior surface of the sealed bag when penetrating the sealed bag; and
a longitudinal support element attached to an internal surface of bag without penetrating the bag and extending essentially parallel to the internal surface of the bag and wherein the longitudinal support element comprises at least one opening; and
wherein the longitudinal support element is disposed substantially opposite the sealing element and the access probe is configured to pass through the at least one opening of the longitudinal support element after penetrating the sealed bag.

20. The container according to claim 19, wherein the access probe is formed integrally with the lid of the container.

21. The container according to claim 19, wherein the lid and a remainder of the container comprise a snap-fit for securing the lid to the remainder of the container, so that the access probe is separate from the sealed bag when the lid is unsecured to the remainder of the container, and so that the access probe pierces the sealed bag when the lid is secured to the remainder of the container.

22. The container according to claim 19, wherein the sealing element is attached to an outer surface of the bag.

23. The container according to claim 19, wherein the sealing element is attached to the access probe.

24. The container according to claim 19, wherein the container further comprises a frame-like structure situated between the sealed bag and the access probe, and wherein the sealing element is attached in the frame-like structure.

25. The container according to claim 24, wherein the sealing element abuts an outer surface of the bag.

26. The container according to claim 19, wherein the longitudinal support element is attached to an internal surface portion of the sealed bag.

27. The container according to claim 26, wherein the support element and the internal surface portion of the sealed bag are made from the same material.

28. The container according to claim 27, wherein the support element and the internal surface portion of the sealed bag are made from polyethylene.

29. The container according to claim 19, wherein an inner wall forming the at least one opening of the longitudinal support element is substantially non-deformable.

30. The container according to claim 19, wherein the container holds a plurality of sealed bags and one or more access probes.

* * * * *

UNITED STATES PATENT AND TRADEMARK OFFICE
CERTIFICATE OF CORRECTION

PATENT NO.        : 9,101,936 B2
APPLICATION NO.   : 12/081996
DATED             : August 11, 2015
INVENTOR(S)       : Herlev Ib Marcher et al.

It is certified that error appears in the above-identified patent and that said Letters Patent is hereby corrected as shown below:

On the Title Page, Item (73), in the Assignee, line 1,
"Bronshol" should read --Brønshøj--.

In The Claims

In claim 7, column 6, line 63,
"non deformable." should read --non-deformable.--.

In claim 19, column 8, line 2,
"surface of bag" should read --surface of the bag--.

Signed and Sealed this
Twenty-fourth Day of May, 2016

Michelle K. Lee
*Director of the United States Patent and Trademark Office*